United States Patent [19]

Bach et al.

[11] 4,322,430

[45] Mar. 30, 1982

[54] AMINO-SUBSTITUTED 4,5,6,7-TETRAHYDRO-1H (OR 2H)-INDAZOLES

[75] Inventors: Nicholas J. Bach; Edmumd C. Kornfeld, both of Indianapolis, Ind.

[73] Assignee: Eli Lilly and Company, Indianapolis, Ind.

[21] Appl. No.: 235,500

[22] Filed: Feb. 19, 1981

Related U.S. Application Data

[63] Continuation of Ser. No. 20,559, Mar. 15, 1979, Pat. No. 4,276,300, which is a continuation-in-part of Ser. No. 5,064, Jan. 22, 1979, abandoned.

[51] Int. Cl.³ .......................................... A61K 31/415
[52] U.S. Cl. ............................................... 424/273 P
[58] Field of Search ...................... 424/273 P, 273 N

[56] References Cited

U.S. PATENT DOCUMENTS 3,520,901  7/1970  Massaroli ............................ 548/359

*Primary Examiner*—Henry R. Jiles
*Assistant Examiner*—Natalia Harkaway
*Attorney, Agent, or Firm*—James L. Rowe; Arthur R. Whale

[57] ABSTRACT

Amino-substituted-4,5,6,7-tetrahydro-1H (or 2H)-indazoles, useful as prolactin inhibitors and in treatment of Parkinson's Syndrome.

1 Claim, No Drawings

AMINO-SUBSTITUTED 4,5,6,7-TETRAHYDRO-1H (OR 2H)-INDAZOLES

CROSS-REFERENCE

This application is a division of Ser. No. 20,559 filed Mar. 15, 1979, now U.S. Pat. No. 4,276,300, which is a continuation-in-part of our copending application Ser. No. 5,064 filed Jan. 22, 1979, now abandoned.

SUMMARY OF THE INVENTION

This invention provides a group of tetrahydro-1H (or 2H)-indazoles of the formulae wherein one of R and $R^1$ is H and the other is $N(R^2)_2$ wherein each $R^2$ is individually H, allyl, methyl, ethyl or n-propyl and pharmaceutically-acceptable acid addition salts thereof formed with non-toxic acids. These compounds and their salts are useful as dopamine agonists for treating Parkinsonism and for inhibiting prolactin secretion. Compounds according to I and II in which one or both $R^2$ groups are hydrogen, while having some dopamine agonist activity, are predominantly useful as intermediates for compounds in which $R^2$ is alkyl or allyl.

Compounds according to I and II above in which one of R and $R^1$ is H and the other is NH—CO—$R^3$ wherein $R^3$ is methyl, ethyl, or n-propyl are also included within the scope of this invention. These compounds and their salts are useful as intermediates.

Compounds represented by I and II are tautomers; i.e., in solution, they exist in dynamic equilibrium with the percent of a given tautomer in the mixture depending on both environment and electronic forces. Formula I above represents a 1H-indazole and Formula II a 2H-indazole.

The pharmaceutically-acceptable acid addition salts of the compounds of this invention wherein one of R and $R^1$ is H and the other is $N(R^2)_2$ and each $R^2$ is individually H, methyl, ethyl, n-propyl or allyl, include salts derived from non-toxic inorganic acids such as: hydrochloric acid, nitric acid, phosphoric acid, sulfuric acid, hydrobromic acid, hydriodic acid, nitrous acid, phosphorous acid and the like, as well as salts derived from non-toxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

Illustrative compounds coming within the scope of Formula I above include:

dl-5-dimethylamino-4,5,6,7-tetrahydro-1H-indazole methane sulfonate.

dl-5-diethylamino-4,5,6,7-tetrahydro-1H-indazole maleate.

dl-6-diallylamino-4,5,6,7-tetrahydro-1H-indazole sulfate.

dl-5-di(n-propyl)amino-4,5,6,7-tetrahydro-1H-indazole hydrochloride.

dl-5-acetamido-4,5,6,7-tetrahydro-1H-indazole.

dl-6-acetamido-4,5,6,7-tetrahydro-1H-indazole.

Illustrative compounds coming within the scope of Formula II include:

dl-5-amino-4,5,6,7-tetrahydro-2H-indazole.

N-methyl-N-allyl dl-5-amino-4,5,6,7-tetrahydro-2H-indazole methanesulfonate.

dl-6-dimethylamino-4,5,6,7-tetrahydro-2H-indazole maleate.

dl-5-propionamido-4,5,6,7-tetrahydro-2H-indazole.

N-methyl-N-ethyl dl-5-amino-4,5,6,7-tetrahydro-2H-indazole hydrochloride.

N-methyl-N-n-propyl dl-5-amino-4,5,6,7-tetrahydro-2H-indazole sulfate.

N-allyl-N-n-propyl dl-5-amino-4,5,6,7-tetrahydro-2H-indazole tartrate.

The presence of a substituent at C-5 or C-6 in the indazole ring introduces a center of assymmetry into those molecules. Thus, compounds represented by Formulas I and II include two optical isomers occurring as a dl pair or racemate. Resolution of a dl pair of this invention into its optical antipodes can be accomplished by procedures known to those skilled in the art.

The compounds of this invention wherein $R^1$ is H and R is N $(R^2)_2$ are prepared according to the following Reaction Scheme I.

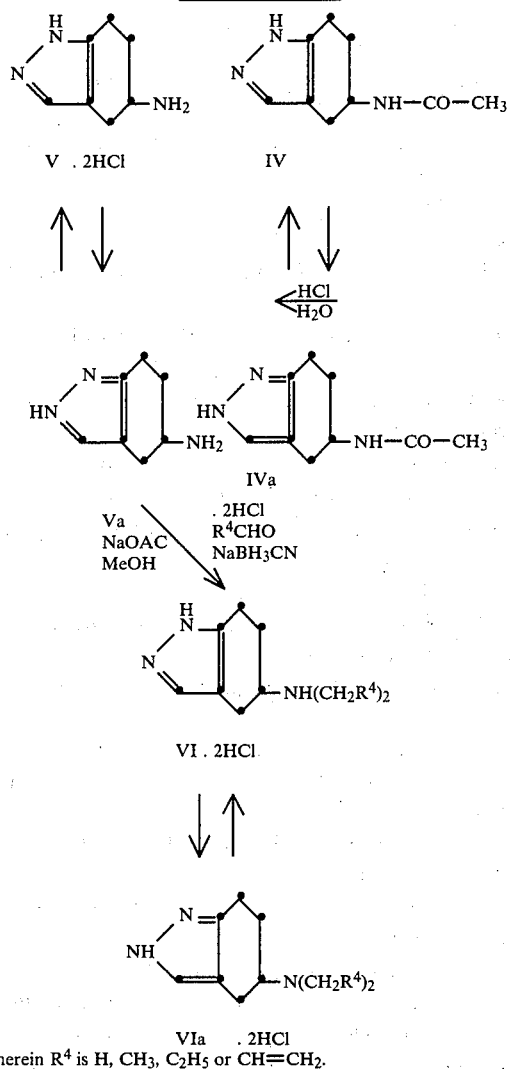

-continued
Reaction Scheme I

V . 2HCl

IV

VIa . 2HCl wherein $R^4$ is H, $CH_3$, $C_2H_5$ or $CH=CH_2$.

In accordance with Reaction Scheme I, 4-acetamidocyclohexanone is reacted with dimethylformamide dimethylacetal. The product of this reaction, 4-acetamido-2-dimethylaminomethylenecyclohexanone (III), reacts with hydrazine hydrate in a suitable inert mutual solvent such as methanol to yield directly dl-5-acetamido-4,5,6,7-tetrahydro-1H-indazole (IV) and its 2H tautomer (IVa), ordinarily isolated as an acid addition salt such as the methane sulfonate or hydrochloride because of the lack of crystallinity of the free base. Hydrolysis of IV and IVa, with aqueous hydrochloric acid for example, yields directly dl-5-amino-4,5,6,7-tetrahydro-1H-indazole and its 2H tautomer as the dihydrochlorides salts (V and Va), compounds of this invention according to formulas I and II above in which R is $NH_2$ and $R^1$ is H. Transformation of this primary amine to compounds of this invention in which R is N(methyl)$_2$, N(ethyl)$_2$, N(n-propyl)$_2$, N(allyl)$_2$ etc. is readily accomplished by reaction with an aldehyde, $R^4CHO$ wherein $R^4$ is H, vinyl, methyl or ethyl, in a reductive alkylation in the presence of sodium cyanoborohydride or other suitable reducing agent.

Compounds according to I and II above in which the $R^2$ groups are dissimilar are prepared by, for example, reducing a C-5 acetamide such as IV or IVa to yield an N-ethyl derivative. Alkylation of this secondary amine by standard procedures such as use of an alkyl halide, for example methyl iodide, yields an N-methyl-N-ethyl amine group at C-5. Additionally, the secondary amine can be acylated as with propionic anhydride, and the resulting propionamide reduced with $LiAlH_4$ to yield an N-ethyl-N-n-propylamine group at C-5. Acylation of the indazole nitrogen, if any, can be selectively reversed.

Compounds of this invention in which $R^1$ is $N(R^2)_2$ and R is H are prepared by a slightly different, though similar, synthetic procedure illustrated in Reaction Scheme II below. In Reaction Scheme II $R^2$ has the same meaning as before and wherein $R^5$ is $(C_1-C_3)$alkyl or benzyl. The term $(C_1-C_3)$alkyl includes methyl, ethyl, n-propyl and isopropyl.

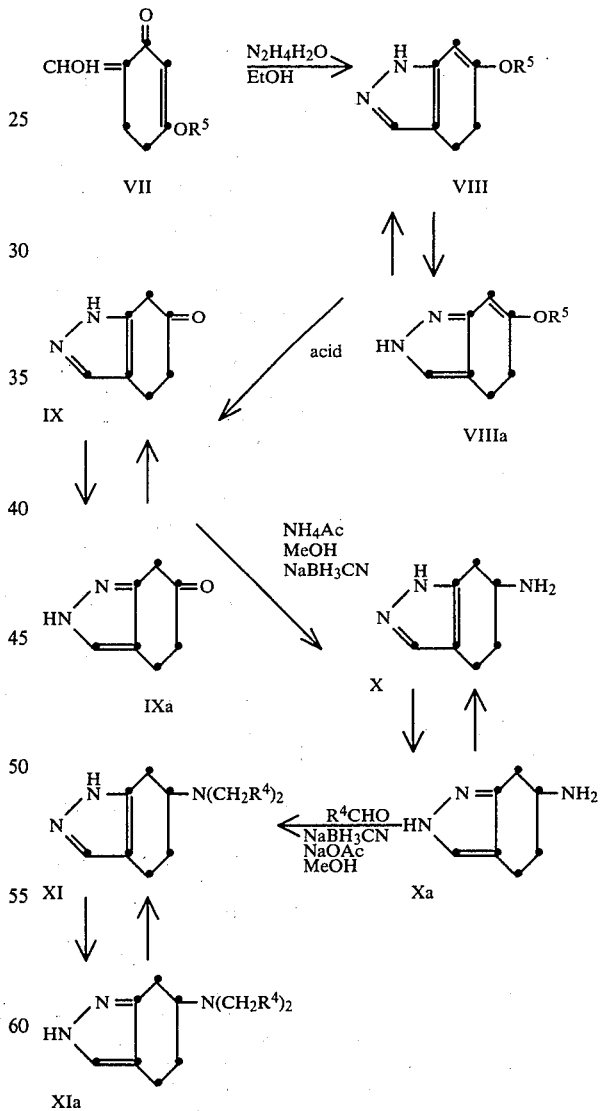

Reaction Scheme II

In accordance with Reaction Scheme II, a 3-enol ether-6-hydroxymethylene-2-cyclohexenone, for example 3-ethoxy-6-hydroxymethylene-2-cyclohexenone, prepared by the method of Wenkert et al. J. Org. Chem., 27, 2278 (1962), is reacted with hydrazine hydrate in a mutual inert solvent such as ethanol to yield dl-6-ethoxy-4,5-dihydro-1H-indazole (VIII) and its 2H tautomer (VIIIa). Hydrolysis with acid, preferably a strong, highly ionized acid such as p-toluenesulfonic, trifluoroacetic, hydrochloric etc., yields dl-6-oxo-4,5,6,7-tetrahydro-1H-indazole (IX) and the 2H tautomer (IXa). Reductive amination of this oxo compound with ammonium acetate and sodium cyanoborohydride, or other suitable organometallic reducing agent of sufficient reducing power, in the presence of a mutual inert solvent yields the corresponding dl-6-amino-4,5,6,7-tetrahydro-1H-indazole, (X) and dl-6-amino-4,5,6,7-tetrahydro-2H-indazole, compounds coming within the scope of formulas I and II above wherein R is H and $R^1$ is $NH_2$.

Preparation of compounds of this invention wherein R is H and $R^1$ is $N(CH_3)_2$, $N(C_2H_5)_2$ or $N(n-propyl)_2$ is carried out by reductively alkylating the 6-amino compound (X) and (Xa) with an aldehyde in the presence of a organometallic reducing agent such as sodium cyanoborohydride in accordance with the procedure set forth in connection with Reaction Scheme I above, to yield the dl-6-dialkyl(or diallyl)amino-4,5,6,7-tetrahydro-1H-indazole (XI) and the corresponding 2H tautomer (XIa). The preparation of compounds in which the 6-amino group is unsymmetically substituted can be accomplished by reacting the primary amine (X and Xa) with one mole of an acid chloride or anhydride to yield the 6-acylamino derivative, reducing the acyl group to an alkyl group (e.g., acetyl→ethyl) with $LiAlH_4$ and then alkylating the thus-formed secondary amine at C-6 with an alkylating agent containing a different alkyl group (e.g., methyl or n-propyl in the above example.)

The novel intermediates represented by VIII and VIIIa and IX and IXa in Reaction Scheme II are prepared by formylating at C-6 an enolether of cyclohexane-1,3-dione.

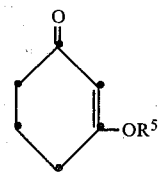

wherein $R^5$ is $(C_1-C_3)$ alkyl or benzyl, using the procedure of Wenkert, et al (loc. cit.) to yield a compound of formula VII. Reaction of VII with hydrazine hydrate yields the tautomers VIII and VIIIa, de-enolization of which with acid gives the keto compounds IX and IXa.

The compounds of this invention have all been named as dl-5(or 6)-amino-4,5,6,7-tetrahydro-1H-indazoles and dl-5(or 6)-amino-4,5,6,7-tetrahydro-2H-indazoles. The presence of the amino group at C-5 or C-6 of the indazole ring produces a center of assymmetry and thus the compounds of this invention are prepared as a racemate or dl mixture. These racemates can be revolved into their respective d and l-isomers by methods available in the art. It is believed that the dopamine agonist activity shown by the racemates of this invention may reside chiefly, if not entirely, in a single stereoisomer. Thus, this invention provides not only dl racemates having dopamine agonist activity but also substantially pure stereoisomers having dopamine agonist activity.

This invention is further illustrated by the following specific examples:

EXAMPLE 1

Preparation of 4-Acetamido-2-dimethylaminomethylenecyclohexanone

A reaction mixture was prepared from 15.5 g. of 4-acetamidocyclohexanone [prepared by the procedure of Fraser and Swingle, *Can. J. Chem.*, 48, 2065 (1970)], 80 g. of the dimethylacetal of dimethylformamide, 1.5 ml. of triethylamine and 500 ml. of benzene. The benzene was distilled therefrom over a 1.5 hour period until the volume was reduced to about ½ of the original volume. An additional 250 ml. of benzene were added. The reaction mixture was heated just below the boiling point of benzene for about 2 hours and was then distilled again until the volume was about one-half of that originally present (250 ml.). The above process was repeated once more except that the volume was reduced to one-third of the original volume (167 ml.). The reaction mixture was then cooled and filtered. The filter cake consisted of 4-acetamido-2-dimethylaminomethylenecyclohexanone formed in the above reaction; weight=6.45 g. Evaporation of the filtrate to dryness yielded a residue, chromatography of a chloroform solution of which over 200 g. of florisil using chloroform containing increasing amounts of methanol (0-5%) as an eluant, yielded pure 4-acetamido-2-dimethylaminomethylenecyclohexanone; m.p.=132°-133° C. (from benzene); yield=5.55 g.; total yield=12 g.

Analysis Calc.: C, 62.83; H, 8.63; N, 13.32; Found: C, 63.07; H, 8.38; N, 13.12.

EXAMPLE 2

Preparation of dl-5-Amino-4,5,6,7-tetrahydro-1H-indazole and dl-5-Amino-4,5,6,7-tetrahydro-2H-indazole A solution was prepared by dissolving 1.46 g. of 4-acetamido-2-dimethylaminomethylenecyclohexanone in 25 ml. of methanol. 0.35 ml. of hydrazine hydrate were added and the resulting mixture stirred at room temperature for about 16 hours. The reaction mixture was concentrated by evaporation in vacuo and a chloroform solution of the residue was chromatographed over 30 g. of florisil using chloroform containing increasing amounts (2-5%) of methanol as the eluant. Fractions shown by TLC to contain a major component different from starting material were combined and the solvent evaporated therefrom in vacuo. 1.5 g. of dl-5-acetamido-4,5,6,7-1H-indazole and its 2H tautomer were obtained. The material was dissolved in anhydrous ethanol to which was added 0.5 ml. of methane sulfonic acid. dl-5-Acetamido-4,5,6,7-tetrahydro-1H-indazole methane sulfonate and dl-5-acetamido-4,5,6,7-tetrahydro-2H-indazole methane sulfonate thus prepared melted at about 190°-2° C.; yield equal 1.61 g.

Analysis Calc.: C, 43.62; H, 6.22; N, 15.26; S, 11.65: Found: C, 43.83; H, 6.37; N, 15.15; S, 11.39.

A solution of 950 mg. of a mixture of dl-5-acetamido-4,5,6,7-tetrahydro-1H-indazole methane sulfonate and the 2H-tautomer methane sulfonate in 50 ml. of 6 N aqueous hydrochloric acid was refluxed under a nitrogen atmosphere for sixty minutes. The reaction mixture was cooled and the volatile constituents removed by evaporation in vacuo. The resulting residue was dissolved in ethanol, and the ethanol solution concentrated and cooled. dl-5-Amino-4,5,6,7-tetrahydro-1H-indazole dihydrochloride and dl-5-amino-4,5,6,7-tetrahydro-2H-indazole dihydrochloride formed in the above reaction crystallized and were separated by filtration; m.p.=260°-70° C.: yield=380 mg.

Analysis Calc.: C, 40.02; H, 6.24; N, 20.00; Cl, 33.75: Found: C, 40.29; H, 5.99; N, 20.12; Cl, 33.63.

EXAMPLE 3

Preparation of
dl-5-Dimethylamino-4,5,6,7-tetrahydro-1H-indazole
and
dl-5-Dimethylamino-4,5,6,7-tetrahydro-2H-indazole.

A reaction mixture was prepared containing 630 mg. of dl-5-amino-4,5,6,7-tetrahydro-1H-indazole dihydrochloride and its 2H tautomer dihydrochloride 410 mg. of sodium acetate, and 75 ml. of ethanol. To this mixture was added 380 mg. of sodium cyanoborohydride followed by 1 ml. of 37% aqueous formalin. The resulting mixture was stirred at ambient temperature for about 17 hours, after which time it was poured into an ice-1 N aqueous hydrochloric acid mixture. The aqueous layer was extracted with chloroform and the chloroform extract discarded. The aqueous layer was then made basic with 14 N aqueous ammonium hydroxide and the resulting alkaline solution extracted several times with a chloroform-isopropanol solvent mixture. The extracts were combined and the combined extracts washed with saturated aqueous sodium chloride and then dried. Evaporation of the solvent yielded 0.43 g. of a residue comprising dl-5-dimethylamino-4,5,6,7-tetrahydro-1H-indazole and dl-5-dimethylamino-4,5,6,7-tetrahydro-2H-indazole formed in the above reaction. NMR of the tautomeric mixture gave characteristic peaks at 142 cps (singlet-aminomethyl) 432 and 440 cps (broad singlet C-3H) using CDCl$_3$. The compounds were further purified by dissolving the residue in 10 ml. of 1 N aqueous hydrochloric acid and diluting this mixture with anhydrous ethanol. This solution was evaporated to dryness in vacuo and the resulting residue crystallized from a methanol/ether solvent mixture. dl-5-Dimethylamino-4,5,6,7-tetrahydro-1H-indazole dihydrochloride and dl-5-dimethylamino-4,5,6,7-tetrahydro-2H-indazole dihydrochloride thus prepared melted at 230°-38° C. with foaming; yield=430 mg.

Analysis Calc.: C, 45.39; H, 7.20; N, 17.64: Found: C, 45.26; H, 7.13; N, 17.46.

Following the above example, but substituting propionaldehyde for formaldehyde, there was prepared a mixture of dl-5-di(n-propyl)amino-4,5,6,7-tetrahydro-1H-indazole and its 2H-tautomer. NMR in CDCl$_3$ gave characteristic peaks at 52 cps (triplet-propyl CH$_3$) and 432 (singlet —C—3H). The dihydrochloride salts of the tautomeric mixture were prepared, melting at 154°-60° C. with foaming; yielded=2.97 g. (from 2.15 g. of starting material).

Analysis Calc.: C, 53.06; H, 8.56; N, 14.28: Found: C, 52.83; H, 8.83; N, 14.30.

EXAMPLE 4

Preparation of
dl-6-Amino-4,5,6,7-tetrahydro-1H-indazole and
dl-6-Amino-4,5,6,7-tetrahydro-2H-indazole A solution was prepared from 5 g. of 3-ethoxy-6-hydroxymethylene-2-cyclohexenone [prepared by the method of Wenkert et al., *J. Org. Chen.*, 27, 2278, (1962)] and 150 ml. of ethanol. 1.9 ml. of hydrazine hydrate were added and the resulting mixture stirred at room temperature under nitrogen atmosphere for 18 hours. The reaction mixture was evaporated in vacuo and the residue dissolved in chloroform. The chloroform solution was chromatographed over 100 g. of florisil using chloroform containing increasing amounts (0–2%) of ethanol as the eluant. Fractions shown by TLC to contain a major spot different from starting material were combined and the solvents evaporated from the combined fractions in vacuo. The resulting residue was crystallized from a mixture of ether and hexane. dl-6-Ethoxy-4,5-dihydro-1H-indazole and its 2H tautomer thus prepared melted at 118°-120° C.; yield=3.64 g.

Analysis Calc.: C, 65.83; H, 7.37; N, 17.06: Found: C, 66.03; H, 7.25; N, 16.81.

A mixture of 3.2 g. of dl-6-ethoxy-4,5-dihydro-1H-indazole and its 2H tautomer and 150 ml. of 1 N aqueous hydrochloric acid were stirred at ambient temperature under a nitrogen atmosphere for 1.25 hours. TLC indicated that a new major spot (not starting material) was present. An infrared spectrum of this major spot showed absorption at 1710 cm.$^{-1}$ indicating formation of a keto group. The reaction mixture was saturated with solid sodium bicarbonate and the aqueous alkaline mixture extracted several times with chloroform. The chloroform solutions were combined and the combined solutions washed with saturated aqueous sodium chloride and then dried. Evaporation of the chloroform yielded a residue which was dissolved in chloroform and chromatographed over 30 g. of florisil using chloroform containing 2% methanol as the eluant. Fractions shown to contain dl-6-oxo-4,5,6,7-tetrahydro-1H-indazole and dl-6-oxo-4,5,6,7-tetrahydro-2H-indazole formed in the above reaction were combined and dissolved in methanol. 0.7 ml. of methane sulfonic acid were added and the resulting mixture diluted to a volume of about 125 ml. with ether. The solution was cooled and the volatile constituents were removed by evaporation in vacuo. The residue was dissolved in ethanol, and the ethanol solution diluted with ether. On cooling an oil formed. The oil was redissolved in ethanol, ether added to the point of incipient precipitation and the mixture allowed to cool. Crystalline dl-6-oxo-4,5,6,7-tetrahydro-1H(and 2H)-indazole methane sulfonate was obtained which melted in the range 95°-105° C. after recrystallization from an ether/ethanol solvent mixture; yield=1.86 g.

Analysis Calc.: C, 41.37; H, 5.21; N. 12.06; S. 13.81: Found: C, 41.57; H, 5.38; N. 11.77; S. 13.53.

Eight grams of dl-6-oxo-4,5,6,7-tetrahydro-1H-indazole hydrochloride plus the hydrochloride of the 2H-tautomer (formed by metathesis from the above methane sulfonate) and 30 g. of ammonium acetate were dissolved in 400 ml. of methanol to which was added 2.9 g. of sodium cyanoborohydride. The reaction mixture was stirred at room temperature under a nitrogen atmosphere for about 1 day after which time it was poured into an excess of 1 N aqueous hydrochloric acid. The aqueous layer was extracted with ether and the ether extract discarded. The aqueous layer was then made basic with dilute aqueous sodium hydroxide and the basic layer extracted several times with a chloroform-isopropanol solvent mixture. The organic extracts were combined and the combined extracts washed with saturated aqueous sodium chloride and then dried. Evaporation of the solvent yielded a residue comprising dl-6-amino-4,5,6,7-tetrahydro-1H-indazole and dl-6-amino- 4,5,6,7-tetrahydro-2H-indazole. The residue was dissolved in 200 ml. of ethanol and the ethanol solution added dropwise with stirring to 7.7 ml. of 12 N aqueous hydrochloric acid. The resulting mixture was concentrated in vacuo to yield an equilibrium mixture of dl-6-amino-4,5,6,7-tetrahydro-1H-indazole dihydrochloride and dl-6-amino-4,5,6,7-tetrahydro-2H-indazole dihydrochloride melting at 275°–280° C. with decomposition after recrystallization from ethanol. Yield=4.20 g.

Analysis Calc.: C, 40.02. H, 6.24; N, 20.00: Found: C, 39.74; H, 6.04; N, 19.80.

Following the procedure of Example 3, dl-6-amino-4,5,6,7-tetrahydro-1H(and 2H)-indazole was alkylated with propionaldehyde and NaBH$_3$CN to yield dl-6-di-(n-propyl)amino-4,5,6,7-tetrahydro-1H(and 2H)-indazole. The free base was a non-crystalline glass; mass spectrum, molecular ion (M+) at 221.

As evidence of the utility of the compounds of this invention in the treatment of Parkinson's Syndrome, it has been found that they affect turning behavior in a test procedure utilizing 6-hydroxydopamine-lesioned rats. In this test, nigro-neostriatal-lesioned rats, prepared by the procedure of Ungerstedt and Arbuthnott, *Brain Res*, 24, 485 (1970) are employed. A compound having dopamine agonist activity, upon injection, causes the rats to turn in circles contralateral to the side of the lesion. After a latency period, which varies from compound to compound, the number of turns is counted over a 15-minute period. The compounds are dissolved in water and the resulting aqueous solution injected into the rat by the intraperitoneal route at a series of dose levels. Table 1 which follows gives the results of these tests. In Table 1, column 1 gives the name of the compound, column 2 the dose, column 3 the percent of rats exhibiting turning behavior and column 4 the average number of turns.

TABLE 1

| | Turning Behavior | | |
| --- | --- | --- | --- |
| Name of Compound | dose level | Percent of rats exhibiting turning behavior | Number of turns |
| dl-5-di-(n-propyl)amino-4,5,6,7-tetrahydro-1H(and 2H)-indazole dihydrochloride | 1 mg/kg | 67 | 48 |
| | 100 mcg/kg | 33 | 6 |
| dl-5-dimethylamino-4,5,6,7-tetrahydro-1H(and 2H)indazole dihydrochloride | 1 mg/kg | 33 | 5 |
| dl-5-amino-4,5,6,7-tetrahydro-1H(and 2H)indazole dihydrochloride | 1 mg/kg | 33 | 7 |
| dl-6-di-(n-propyl)amino-4,5,6,7-tetrahydro-1H(and 2H)-indazole dihydrochloride | 1 mg/kg | 100 | 98 |
| | 250 mcg/kg | 50 | 30 |
| | 100 mcg/kg | 0 | — |

The compounds of this invention are also useful as prolactin inhibitors and as such can be employed in the treatment of inappropriate lactation, such as postpartum lactation and galactorrhea. As evidence of their utility in the treatment of diseases in which it is desirable to reduce the prolactin level, the compounds of this invention have been shown to inhibit prolactin according to the following procedure.

Adult male rats of the Sprague-Dawley strain weighing about 200 g. were housed in an air-conditioned room with controlled lighting (lights on 6 a.m.–8 p.m.) and fed lab chow and water ad libitum. Each rat received an intraperitoneal injection of 2.0 mg. of reserpine in aqueous suspension 18 hours before administration of the indazole. The purpose of the reserpine was to keep prolactin levels uniformly elevated. The compounds under test were dissolved in water and were injected intraperitoneally at doses ranging from 5 mg/kg down to 50 mcg/kg. Each compound was administered at each dose level to a group of 10 rats, and a control group of 10 intact males received an equivalent amount of solvent. One hour after treatment all rats were killed by decapitation, and 150 μl aliquots of serum were assayed for prolactin.

The difference between the prolactin level of the treated rats and prolactin level of the control rats divided by the prolactin level of the control rats gives the percent inhibition of prolactin secretion attributable to the compounds of this invention. These inhibition percentages are given in Table 2 below. In the table, column 1 gives the name of the compound; and columns 2–4 the percent prolactin inhibition at the given dose level.

TABLE 2

| Percent Inhibition of Prolactin at a Given Dose Level | | | |
| --- | --- | --- | --- |
| Name of Compound | 5 mg/kg | 500 mcg/kg | 50 mcg/kg |
| dl-5-di-(n-propyl)amino-4,5,6,7-tetrahydro-1H(and 2H)indazole dihydrochloride | 94 | 66 | 1 |
| dl-5-dimethylamino-4,5,6,7-tetrahydro-1H(and 2H)indazole dihydrochloride | 73 | 30 | 31 |
| dl-6-di-(n-propyl)amino-4,5,6,7-tetrahydro-1H(and 2H)indazole dihydrochloride | — | — | 31 |

In using the compounds of this invention to inhibit prolactin secretion or to treat Parkinson's syndrome or for other pharmacologic action, a compound according to Formulas I and II above, or a salt thereof with a pharmaceutically-acceptable acid, is administered to a subject suffering from Parkinsonism, or in need of having their prolactin level reduced, in an amount effective to alleviate some of the symptoms of Parkinsonism or to reduce an elevated prolactin level. Oral administration is preferred. If parenteral administration is used, the injection is preferably by the subcutaneous route using an appropriate pharmaceutical formulation. Other modes of parenteral administration such as intraperitoneal, intramuscular, or intravenous routes are equally effective. In particular, with intravenous or intramuscular administration, a water soluble pharmaceutically-acceptable salt is employed. For oral administration, a compound according to Formulas I and II either as the free base or in the form of a salt thereof can also be mixed with standard pharmaceutical excipients and loaded into empty telescoping gelatin capsules or pressed into tablets. The oral dosage should be in the range 0.01–10 mg/kg of mammalian body weight and the parenteral dose in the range 0.0025 to 2.5 mg/kg. The LD$_{50}$ of dl-5-di(n-propyl)amino-4,5,6,7-tetrahydro-1H(and 2H)-indazole dihydrochloride is between 100 and 300 mg/kg by the intraperitoneal route in the mouse. Doses of 10 and 30 mg/kg are not fatal but a 30 mg/kg dose produces some undesirable side effects.

We claim:

1. A method of treating Parkinson's Syndrome which consists of administering to a human suffering from Parkinson's Syndrome and in need of treatment, a dose of a tautomer of the formula

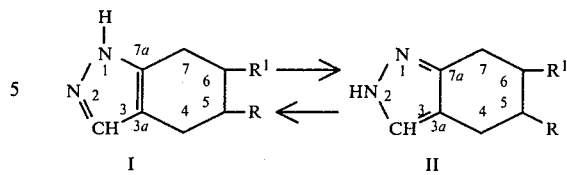

wherein one of R and $R^1$ is H and the other is $N(R^2)_2$ wherein each $R^2$ is individually H, allyl, methyl, ethyl or n-propyl and pharmaceutically-acceptable acid addition salts thereof formed with non-toxic acids, effective to alleviate some or all of the manifestations of Parkinson's Syndrome.

* * * * *